US00PP28541P3

(12) United States Plant Patent
Meilland

(10) Patent No.: US PP28,541 P3
(45) Date of Patent: Oct. 24, 2017

(54) FLORIBUNDA ROSE PLANT NAMED 'MEISCARLEBO'

(50) Latin Name: *Rosa hybrida*
Varietal Denomination: Meiscarlebo

(71) Applicant: The Conard-Pyle Company, West Grove, PA (US)

(72) Inventor: Alain A. Meilland, Antibes (FR)

(73) Assignee: The Conard-Pyle Company, West Grove, PA (US)

( * ) Notice: Subject to any disclaimer, the term of this patent is extended or adjusted under 35 U.S.C. 154(b) by 161 days.

(21) Appl. No.: 14/756,087

(22) Filed: Jul. 30, 2015

(65) Prior Publication Data

US 2017/0006746 P1 Jan. 5, 2017

(30) Foreign Application Priority Data

Jul. 3, 2015 (QZ) ..... PBR 2015/1556

(51) Int. Cl.
*A01H 5/02* (2006.01)

(52) U.S. Cl.
USPC ..... Plt./142

(58) Field of Classification Search
USPC ..... Plt./101, 141, 142
See application file for complete search history.

*Primary Examiner* — Susan McCormick Ewoldt
*Assistant Examiner* — Karen Redden
(74) *Attorney, Agent, or Firm* — Buchanan Ingersoll & Rooney PC

(57) ABSTRACT

A new and distinct Floribunda rose plant is provided that commonly commences blooming medium in the season and forms abundantly and substantially continuously attractive cherry red very double blossoms. The growth habit bushy. Strong very dense vegetation is formed having a glossy aspect on the upper surface. The dark green vegetation contracts nicely with the blossom coloration. Tolerance to disease during observations to date has been very good particularly with respect to black spot. The plant is well suited for providing attractive ornamentation in parks and gardens.

1 Drawing Sheet

Figures 1, 2, 3, 4, 5, 6, 7, 8, 9, 10, 11, 12, 13, 14, 15:
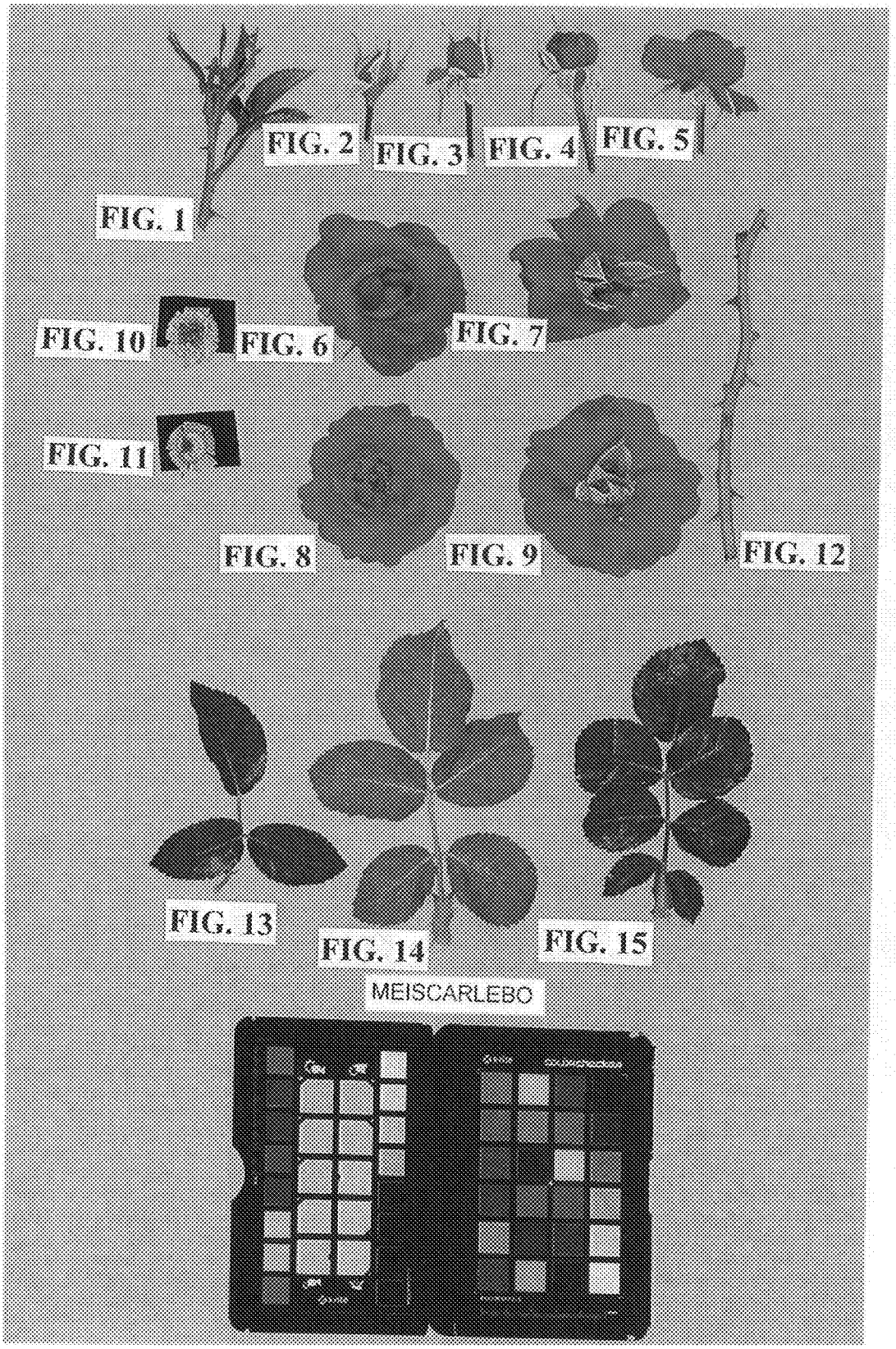

Botanical/commercial classification: *Rosa hybrida*/Floribunda Rose Plant.

Varietal denomination: cv. 'Meiscarlebo'.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the 'Noawel' variety (non-patented in the United States). The male parent (i.e., the pollen parent) was the product of the cross of the 'Kormax' variety (non-patented in the United States) and the 'Meinoiral' variety (non-patented in the United States).

The parentage of the new variety can be summarized as follows:

'Noawel'×('Kormax'×'Meinoiral').

The seeds resulting from the above pollination were sown and small plants were obtained which were physically and biologically different from each other. Selective study resulted in the identification of a single plant of the new variety.

It was found that the new Floribunda rose plant of the present invention:

(a) displays a bushy growth habit with strong vegetation,
(b) forms in abundance on a substantially continuous basis attractive cherry red very double blossoms,
(c) exhibits very dense dark green foliage with a glossy aspect on the upper surface that contrasts nicely with the blossom coloration, (d) exhibits excellent tolerance to disease particularly with respect to black spot, and
(e) is well suited for providing attractive ornamentation in parks and gardens.

The blooming tends to commence medium in the season during observations to date.

The new variety well meets the needs of the horticultural industry and can be grown to advantage in the landscape where attractive ornamentation is to be provided.

The new variety can be readily distinguished from its ancestors. For instance, the 'Noawel' parental variety commonly forms blossoms having only approximately 9 to 16 petals. The 'Kormax' variety commonly forms red blossoms having only approximately 6 petals, and the 'Meinoiral' variety forms dissimilar pink blossoms. The new variety is more compact than the pollen parent, i.e., ('Kormax'× 'Meinoiral').

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meiscarlebo'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one and one-half year of age and were observed during June while growing outdoors on their own roots at Le Cannet des Maures, Var, France. Comparative standard color information is provided at the bottom of the photograph.

FIG. 1—illustrates a specimen of a young shoot;

FIG. 2—illustrates a specimen of a floral bud at the opening of the sepals;

FIG. 3—illustrates a specimen of a floral bud wherein the sepals are more fully open;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a more fully open flower—plan view—obverse;

FIG. 9—illustrates a specimen of a more fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a leaf with three leaflets—plan view—upper surface;

FIG. 14—illustrates a specimen of a leaf with five leaflets—plan view—under surface; and FIG. 15—illustrates a specimen of a leaf with seven leaflets—plan view—upper surface;

DETAILED BOTANICAL DESCRIPTION

The chart used in the identification of the colors is that of The Royal Horticultural Society (R.H.S. Colour Chart). The description is based on the observation of one and one-half year-old plants during June while growing outdoors on their own roots at Le Cannet des Maures, Var, France.

Class: Floribunda.

Plant:

*Growth habit*.—Bushy.

*Height*.—Commonly approach approximately 70 cm on average.

*Width*.—Commonly approach approximately 100 cm on average.

Branches:

*Color*.—Young stems: near Yellow-Green Group 146B. Adult wood: near Yellow-Green Group 146B.

*Thorns*.—On young stems: Configuration: with an obovate base. Quantity: approximately 11 on average on a stem length of 10 cm. Length: approximately 7 mm on average. Color: near Yellow-Green Group 144C and more or less suffused with near Greyed-Orange Group 175A. On adult stems-long prickles: Configuration: curved downwards on the upper surface and slightly concave on the under surface with an obovate base. Quantity: approximately 10 on average on a stem length of 10 cm. Length: approximately 7 mm on average. Color: near Greyed-Yellow Group 162C. On adult stems-small prickles: Configuration: curved downwards on the upper surface with an obovate base. Quantity: approximately 5 on average on a stem length of 10 cm. Length: approximately 3 mm on average. Color: near Greyed-Yellow Group 162C.

Leaves:

*Stipules*.—Adnate, pectinate, rather broad, approximately 1.5 cm in length on average, approximately 2 mm in width on average, near Yellow-Green Group 147A on the upper surface, and near Green Group 143C on the under surface.

*Petioles*.—Upper surface: near Yellow-Green Group 147A in coloration. Under surface: near Green Group 143A in coloration. Texture: slightly glandular on the upper surface, and with many small prickles on the under surface. Length: approximately 3.1 cm on average. Diameter: approximately 1.5 to 2 mm on average.

*Rachis*.—Upper surface: near Green Group 137A in coloration. Under surface: near Yellow-Green Group 144B in coloration. Diameter: approximately 1 to 2 mm on average.

*Leaflets*.—Number 3, and most often 5 and 7. General appearance: very dense with a glossy aspect on the upper surface. Shape: generally elliptical with an acute tip and a rounded base. Size: the terminal leaflets commonly are approximately 5.2 cm in length on average and approximately 3.7 cm in width on average. Serration: slightly denticulate, small and single (as illustrated). Texture: physically firm and leathery with a glossy upper surface. Color (young foliage): Upper surface: near Green Group 137A. Under surface: near Yellow-Green Group 146B. Color (adult foliage): Upper surface: near Yellow-Green Group 147A, with venation near Yellow-Green Group 147C. Under surface: near Yellow-Green Group 147B, with venation near Yellow-Green Group 144B.

Inflorescence:

*Number of flowers*.—Commonly approximately 5 to 15 blossoms per stem.

*Peduncle*.—Pubescent, approximately 3 to 4 cm in length on average, approximately 3 mm in diameter on average, and near Yellow-Green Group 144A and more or less suffused with near Greyed-Orange Group 175A in coloration.

*Sepals*.—Upper surface: tomentose and near Yellow-Green Group 148B in coloration. Under surface: smooth and near Yellow-Green Group 144A suffused with near Greyed-Orange Group 175A in coloration. Shape: longish and narrow, and somewhat upright at the base. Size: approximately 2.4 cm in length on average, and approximately 9 mm in width at the widest point on average. Number: five on average.

*Buds*.—Shape: substantially conical. Size: small. Length: approximately 2 cm on average. Width: approximately 1.3 mm at the widest point on average. Color as calyx breaks: Upper surface: near Red Group 44A more or less suffused with near Red Group 45A. Under surface: near Red Group 45B more or less suffused and margined with near Red Group 45A.

*Flower*.—Shape: cup-shaped. Diameter: approximately 8 cm on average. Color (in the course of opening): Upper surface: near Red Group 45C more or less suffused and margined with near Red Group 45A. Under surface: near Red Group 46B more or less suffused and margined with near Red Group 45A. Color (open flower): Upper side: near Red Group 45C more or less suffused and margined with near Red Group 45A. Under side: near Red Group 46C more or less suffused and margined with near Red Group 45A. Fragrance: none detected. Petal number: approximately 63 on average under normal growing conditions. Petal shape: with a substantially rounded tip and an obtuse base. Petal texture: leathery and somewhat firm. Petal length: approximately 3.5 cm on average. Petal width: approximately 3.4 cm on average. Petal arrangement: imbricated, and without petaloids. Petal drop: good with the petals commonly detaching cleanly before drying. Stamen number: approximately 166 on average. Anthers: regularly arranged around the styles, approximately 1 mm in size on average, and near Greyed-Orange Group 164B in coloration. Filaments: approximately 5 mm in length on average, and near Red-Purple Group 63A in coloration. Pollen: none available for observation. Pistils: approximately 62 on average. Stigmas: approximately 1 mm in size on average, and near Greyed-Orange Group 172B in coloration. Styles: approximately 8 mm in length on average, and near Greyed-Purple Group 181A in coloration. Receptacle: smooth, funnel-shaped in longitudinal section, approximately 1 cm in length on average, approximately 9 mm in width on average at the widest point, and near Yellow-Green Group 144A more or less suffused with near Greyed-Orange Group 175A in coloration. Hips/seeds: none observed.

Development:

*Vegetation*.—Strong.

*Blooming*.—Medium season, very abundant and substantially continuous, typical period is from May up to November.

*Tolerance to disease*.—Very good, particularly with respect to black spot.

The new 'Meiscarlebo' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a bushy growth habit with strong vegetation, (b) forms in abundance on a substantially continuous basis attractive cherry red very double blossoms, (c) exhibits very dense dark green foliage with a glossy aspect on the upper surface that contrasts nicely with the blossom coloration, (d) exhibits excellent tolerance to disease particularly with respect to black spot, and (e) is well suited for providing attractive ornamentation in parks and gardens;

substantially as shown and described.

* * * * *

MEISCARLEBO